(12) United States Patent
Sommer

(10) Patent No.: US 7,894,880 B2
(45) Date of Patent: Feb. 22, 2011

(54) MEASUREMENT OF RENAL EXTRACTION FRACTION USING CONTRAST ENHANCED COMPUTED TOMOGRAPHY

(75) Inventor: Graham Sommer, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1730 days.

(21) Appl. No.: 10/693,068

(22) Filed: Oct. 23, 2003

(65) Prior Publication Data

US 2005/0090736 A1    Apr. 28, 2005

(51) Int. Cl.
*A61B 5/05* (2006.01)
(52) U.S. Cl. .............. 600/431; 424/9.322; 424/9.52; 424/9.4; 424/1.85; 378/4; 378/6; 378/8; 378/51; 378/52
(58) Field of Classification Search .......... 424/9.322, 424/9.52, 9.4, 1.85; 378/4, 6, 8, 51, 52, 53; 600/431
See application file for complete search history.

(56) References Cited

U.S. PATENT DOCUMENTS

| | | | |
|---|---|---|---|
| 4,573,181 A * | 2/1986 | Gronberg et al. .............. 378/45 |
| 5,846,517 A * | 12/1998 | Unger ........................ 424/9.52 |
| 6,071,494 A * | 6/2000 | Unger ........................ 424/9.4 |
| 6,122,540 A | 9/2000 | Katzberg et al. |
| 6,226,352 B1 * | 5/2001 | Salb ......................... 378/98.9 |
| 6,506,364 B1 * | 1/2003 | Simon et al. ............... 424/1.85 |
| 6,733,744 B1 * | 5/2004 | Achilefu et al. ............. 424/9.6 |
| 6,852,842 B2 * | 2/2005 | Brechbiel et al. ............ 534/15 |

OTHER PUBLICATIONS

Bentley et al, Measurement of Renal Perfusion and Blood Flow with Fast Computed Tomography, 1994, Circulation Research, 74:945-951.*
Lerman et al, The Development of X-ray Imaging to Study Renal Function, 1999, Kidney International, vol. 55; 400-416.*
Quinn et al , An alternative Contrast Medium for CT, Journal of Computer Assisted Tomography, 1994, 18(4); 634-6.*
Katzberg et al., "Glomerular Filtration Response to Acute Ureteral Obstruction in the Dog," The Journal of Urology, vol. 134, Nov. 1985, pp. 1007-1010.

* cited by examiner

*Primary Examiner*—Brian Casler
*Assistant Examiner*—Joel M Lamprecht
(74) *Attorney, Agent, or Firm*—Beyer Law Group LLP

(57) ABSTRACT

Renal extraction fraction (EF) is determined through use of computed tomography (CT) measurements of arterial blood before and after injection of a radiographic contrast agent into the blood and CT measurements of renal vein blood after injection of the radiographic contrast agent.

16 Claims, No Drawings

MEASUREMENT OF RENAL EXTRACTION FRACTION USING CONTRAST ENHANCED COMPUTED TOMOGRAPHY

The U.S. government has rights in the claimed invention pursuant to NIH grant no. R01 DK48051 to Stanford University.

BACKGROUND OF THE INVENTION

This invention relates generally to renal function in a living subject, and more particularly the invention relates to measuring renal extraction fraction using computed tomography (CT).

Renal extraction fraction (EF) is an important physiologic measurement of the function of the kidneys in a living subject. Clearance techniques are classically used to measure renal physiologic parameters such as EF, and the direct measurement of clearance can be made through the collection of multiple urine and blood samples for determining the filtration of markers by the kidneys. However, these conventional clearance techniques have many disadvantages and require timed urine collection.

Katzberg et al., U.S. Pat. No. 6,122,540 proposes a method for measurement of renal filtration through use of magnetic resonance imaging. The measurement of renal plasma flow and filtration fraction includes measuring longitudinal spin relaxation time (T1) of blood with a contrast agent and with blood with an injected longitudinal spin relaxation time contrast agent. More specifically, T1 of blood flow into the kidney and T1 of post filtered blood flow out of the kidney are measured.

The present invention is directed to measuring renal extraction fraction through use of contrast enhanced CT using x-ray transmission measurements of blood with and without contrast agents.

SUMMARY OF THE INVENTION

In accordance with the invention, a rapid, non-invasive measurement of renal function in a single kidney is realized through use of CT measurements. CT scans in regions of interest (ROI) are made before administering an x-ray contrast agent and after administering the x-ray contrast agent. Extraction fraction is then calculated using the measured CT or x-ray transmission numbers for the regions of interest.

The invention and objects and features thereof will be more readily apparent from the following description and appended claims.

DETAILED DESCRIPTION OF ILLUSTRATIVE EMBODIMENTS

The invention utilizes x-ray transmission numbers, or CT numbers, to measure renal function in a living subject.

Renal extraction fraction (EF), which is also termed the extraction ratio or filtration fraction, is that proportion of the plasma entering the glomerulus which is actually filtered across the glomerular membrane into Bowman's space. Extraction fraction is an important renal physiologic parameter, which averages from 15% to 20% under normal conditions.

Whereas clearance techniques are classically used to measure renal physiologic parameters such as EF, it has been shown that accurate determination is possible by direct measurement of the concentration of filtration markers in renal arteries and renal veins. Using such techniques, the extraction fraction may be defined as:

$$EF = \frac{C_A - C_V}{C_A} \quad [1]$$

where $C_A$ is the concentration of a filtration marker in the systemic arterial blood entering the kidney, and $C_V$ is the corresponding concentration in the renal venous blood. Standard radiographic contrast agents, including iothalamate and iohexol, may be used as filtration markers since they are freely filtered by the kidney, and neither secreted nor reabsorbed. Assuming linear increase in CT number with concentration of contrast agent, $C_A$ will be proportional to the increase in CT number of the systemic arterial blood following contrast injection, or $CT_A$-$CT_{PRE}$, where $CT_{PRE}$ and $CT_A$ are the pre- and post- contrast CT numbers of the systemic arterial blood. Similarly, $CT_V$ will be proportional to $CT_V$-$CT_{PRE}$, where $CT_V$ is the post-contrast CT number of a renal vein. Substituting into equation [1] yields:

$$EF = \frac{CT_A - CT_V}{CT_A - CT_{PRE}}. \quad [2]$$

In a retrospective study, CT scans of 10 adult patients (mean age 58.1 years, 7 female) having no known renal disease, and one 45 year old male patient with unilateral renal obstruction were studied. All patients had precontrast scans followed by injection of 120 ml. of iohexol (Omnipaque 350, Amersham Health, Princeton, N.J.) at 2 ml/sec., and enhanced scans through the kidney vasculature, delayed for 3 to 5 minutes after the end of the contrast injection. CT section thickness varied from 2.5 mm to 5 mm. Pre- and post-contrast delayed images were evaluated using ROI measurements taken within the abdominal aorta in the region of the renal vessels, and within right and left renal veins. Multiple measurements, one from each of several axial scans, within each vessel were obtained, varying from 2 to 4 measurements for each renal vein, and 4-8 measurements for the abdominal aorta. Mean CT number values were subsequently computed for each vessel. EF values for the right and left kidneys in each subject were then computed for each patient using equation [2] above. Propagation of error was used to estimate the standard deviation in the computed EF values, as expressed in:

$$\sigma_{EF} = \frac{1}{CT_A - CT_{PRE}} \sqrt{(1-EF)^2 \sigma^2_{CT_A} + \sigma^2_{CT_V} + EF^2 \sigma^2_{CT_{PRE}}} \quad [3]$$

where $\sigma^2_{CT_A}$, $\sigma^2_{CT_V}$, and $\sigma^2_{CT_{PRE}}$ are the variances in the mean values for each region.

Mean arterial enhancement averaged 78.3 HU, and renal venous enhancement averaged 68 HU for all patients studies. Calculated values for EF in the right and left kidneys of the 10 patients with no history of renal disease are summarized in Table 1 below. The weighted mean values (weighted by the inverse of the variance (7)) for right and left renal EF (mean±SD) were 12.6±1.0% and 12.3±1.3% respectively, compared to the accepted value of from 15-20%. While EF was symmetric in most patients, the patient with renal obstruction had markedly and significantly (p=0.0019, 2-tailed test) decreased EF in the obstructed left kidney (9.7±4.0%) compared to the unobstructed right kidney (29.6±5.6%).

TABLE 1

Calculated Extraction Fractions (EF) ± s.d. for normal subjects

| Patient Age/sex | Right Renal EF | Left Renal EF |
|---|---|---|
| 78/M | 16.2 ± 4.6% | 17.7 ± 4.7% |
| 50/F | 10.6 ± 4.5% | 8 ± 3.2% |
| 56/F | 18.8 ± 2.8% | 7.7 ± 3.1% |
| 71/F | 13.3 ± 3.1% | 7.7 ± 5.3% |
| 60/F | 8.3 ± 9.6% | 7.7 ± 6.3% |
| 44/M | 16.2 ± 11.6% | 9.1 ± 1.5% |
| 58/F | 7.6 ± 1.6% | 7.8 ± 2.6% |
| 41/F | 16.8 ± 3.4% | 21.1 ± 1.7% |
| 42/M | 16.7 ± 2.2% | 22.2 ± 3.0% |
| 81/F | 8 ± 5.4% | 8.3 ± 1.9% |
| Mean ± s.d. | 12.6 ± 1.0% | 12.3 ± 1.3% |

Values of EF reasonably in accord with accepted values were obtained in the 10 patients having no history of renal disease, indicating the potential of the present technique of EF measurement to complement standard contrast-enhanced renal CT examination with readily-computed EF values. The method employed is somewhat analogous to techniques described for measuring EF by MRI using T1 values of blood in systemic arterial and renal venous blood following gadolinium-DTPA injection. A number of sources of potential error must be minimized to optimize accuracy of EF determination. In addition to statistical noise in the CT images, important potential sources of error include contrast bolus effects, and volume-averaging affecting ROI measurements. It is important to wait a suitable time, likely several minutes, after the contrast bolus to allow for equilibrium of contrast media within the systemic circulation prior to enhanced scanning. If the measurements are obtained too early, before equilibrium is reached, differences between systemic arterial and renal venous contrast levels will likely reflect a combination of bolus and glomerular filtration effects, rather than filtration alone. Volume averaging effects in ROI measurement, particularly in the renal veins, could be a significant source of error due to partial inclusion of adjacent retroperitoneal fat or arterial regions along with the renal veins. Such volume averaging effects can likely be minimized y using thinner CT sections, and exercising care to exclude arterial branches adjacent to the renal veins, possibly by reference to an arterial phase CT when available.

The very asymmetric EF values obtained in the patient with unilateral renal obstruction are consistent with the results of prior studies in which marked decrease in EF was documented over time, in a canine model of ureteral obstruction. See Katzberg, R W, Morris T W, DiMarco P L et al., "Glomerular Filtration Response to Acute Ureteral Obstruction in the Dog," J Urol 1985; 134:1007-1010. This case indicates the potential of CT measurement to provide quantitative EF estimates of renal function, which can provide a useful complement to the morphologic data provided by CT. Recent studies have also found significant decrease in EF in renal ischemia, in an animal model of unilateral renal artery stenosis. See Coulam C H, Lee J H, Wedding K L et al., "Noninvasive measurement of Extraction Fraction and Single-Kidney Glomerular Filtration Rate with MR Imaging in Swine with Surgically Created Renal Arterial Stenoses," Radiology 2002; 223:76-82. Renal extraction fraction values readily calculated from CT scans may prove useful in evaluating the degree of renal dysfunction due to obstructive uropathy, renovascular disease, and other causes.

While the invention has been described with reference to specific embodiments, the description is illustrative of the invention and not to be construed as limiting the invention. For example, gadolinium-DTPA, generally used with MRI as a contrast agent, can also be used as a contrast agent in practicing the invention. Thus, various modifications and applications may occur to those skilled in the art without departing from the true spirit and scope of the invention as defined by the appended claims.

What is claimed is:

1. A method of measuring renal extraction fraction (EF) in a living subject using computed tomography comprising the steps of:
    a) obtaining a CT number ($CT_{PRE}$) of arterial blood prior to addition of a radiographic contrast agent to the blood,
    b) providing a radiographic contrast agent to the blood,
    c) obtaining a CT number ($CT_A$) of arterial blood after addition of the radiographic contrast agent to the blood,
    d) obtaining a CT number ($CT_V$) of blood in a renal vein after addition of the agent to the blood, and
    e) determining renal extraction fraction (EF) from the obtained CT numbers.

2. The method as defined by claim 1 wherein renal extraction fraction (EF) is given by:

$$EF = \frac{CT_A - CT_V}{CT_A - CT_{PRE}}.$$

3. The method as defined by claim 2 wherein step b) includes providing iohexol.

4. The method as defined by claim 2 wherein step b) includes providing iothalamate.

5. The method as defined by claim 2 wherein step b) includes providing gadolinium-DTPA.

6. The method as defined by claim 1 wherein step b) includes providing iohexol.

7. The method as defined by claim 1 wherein step b) includes providing iothalamate.

8. The method as defined by claim 1 wherein step b) includes providing gadolinium-DTPA.

9. A method of determining renal extraction fraction (EF) for a kidney in a living subject, using a computed tomography (CT) apparatus comprising the steps of:
    a) obtaining a measure of x-ray transmission through arterial blood prior to addition of a radiographic contrast agent to the blood, using the CT apparatus,
    b) providing a radiographic contrast agent to the blood,
    c) obtaining a measure of x-ray transmission through arterial blood after addition of the radiographic contrast agent to the blood, using the CT apparatus,
    d) obtaining a measure of x-ray transmission through renal vein blood after addition of the radiographic contrast agent to the blood, and
    e) determining renal extraction fraction from the measures of x-ray transmission in steps a), and c), and d).

10. The method as defined by claim 9 wherein the measures of x-ray transmission are obtained using computed tomography (CT).

11. The method as defined by claim 10 wherein the measures of x-ray transmission are CT numbers.

12. The method as defined by claim 10 wherein the radiographic contrast agent is selected from the group consisting of iohexol, iothalamate, and gadolinium-DTPA.

13. The method as defined by claim 9 wherein the radiographic contrast agent is selected from the group consisting of iohexol and iothalamate.

14. The method as defined by claim 1 wherein the CT numbers ($CT_{PRE}$, $CT_A$, $CT_V$) are each calculated as a mean value of measured image intensities for a plurality of voxels at different locations in one or more axial CT scans.

15. The method as defined by claim 14 wherein the CT number ($CT_V$) of venous blood is calculated using voxels selected in a venous region to exclude arterial regions.

16. The method as defined by claim 14 wherein the renal function is calculated based on a difference between CT numbers.

* * * * *

UNITED STATES PATENT AND TRADEMARK OFFICE
CERTIFICATE OF CORRECTION

PATENT NO. : 7,894,880 B2  
APPLICATION NO. : 10/693068  
DATED : February 22, 2011  
INVENTOR(S) : Graham Sommer Page 1 of 1

It is certified that error appears in the above-identified patent and that said Letters Patent is hereby corrected as shown below:

In the Specification

Please replace Column 1, Line 5-7 with

--FEDERALLY-SPONSORED RESEARCH OR DEVELOPMENT  
This invention was made with Government support under contract DK048051 awarded by the National Institutes of Health. The Government has certain rights in this invention.--

Signed and Sealed this  
Ninth Day of July, 2013

Teresa Stanek Rea  
*Acting Director of the United States Patent and Trademark Office*